(12) United States Patent
Bova et al.

(10) Patent No.: US 6,546,279 B1
(45) Date of Patent: Apr. 8, 2003

(54) COMPUTER CONTROLLED GUIDANCE OF A BIOPSY NEEDLE

(75) Inventors: Frank J. Bova, Gainesville, FL (US); William A. Friedman, Gainesville, FL (US)

(73) Assignee: University of Florida, Gainesville, FL (US)

( * ) Notice: Subject to any disclaimer, the term of this patent is extended or adjusted under 35 U.S.C. 154(b) by 6 days.

(21) Appl. No.: 09/975,200

(22) Filed: Oct. 12, 2001

(51) Int. Cl.⁷ .................................................. A61B 5/05
(52) U.S. Cl. ................. 600/429; 600/410; 600/411; 600/417; 600/424; 600/428; 600/434; 600/437; 600/439; 606/130
(58) Field of Search ................................ 600/424, 410, 600/407, 411, 414, 417, 425, 429, 437, 439, 473, 476, 434; 606/130

(56) References Cited

U.S. PATENT DOCUMENTS

| | | |
|---|---|---|
| 4,350,159 A | 9/1982 | Gouda |
| 4,455,609 A | 6/1984 | Inamura et al. |
| 4,750,487 A | 6/1988 | Zanetti |
| 4,869,247 A | 9/1989 | Howard, III et al. |
| 5,027,818 A | 7/1991 | Bova et al. |
| 5,095,501 A | 3/1992 | Kobayashi |
| 5,125,888 A | 6/1992 | Howard et al. |
| 5,163,076 A | 11/1992 | Koyama |
| 5,189,687 A | 2/1993 | Bova et al. |
| 5,313,844 A | 5/1994 | Kadlicko |
| 5,314,432 A | 5/1994 | Paul |
| 5,339,812 A | 8/1994 | Hardy et al. |
| 5,368,049 A | 11/1994 | Raman et al. |
| 5,526,822 A | 6/1996 | Burbank et al. |
| 5,531,227 A | 7/1996 | Schneider |
| 5,588,430 A | 12/1996 | Bova et al. |
| 5,772,594 A | 6/1998 | Barrick |
| 5,799,055 A | 8/1998 | Peshkin et al. |
| 5,891,034 A * | 4/1999 | Bucholz .................. 600/426 |
| 5,893,832 A | 4/1999 | Song |
| 5,916,163 A | 6/1999 | Panescu et al. |
| 5,954,647 A | 9/1999 | Bova et al. |
| 6,050,724 A | 4/2000 | Schmitz et al. |
| 6,076,008 A * | 6/2000 | Bucholz .................. 600/427 |
| 6,129,668 A * | 10/2000 | Haynor et al. ........... 600/424 |
| 6,159,221 A | 12/2000 | Chakeres |
| 6,236,875 B1 * | 5/2001 | Bucholz et al. ......... 600/407 |
| 6,246,898 B1 * | 6/2001 | Vesely et al. ............ 600/424 |
| 6,263,230 B1 * | 7/2001 | Haynor et al. ........... 600/424 |
| 6,314,310 B1 * | 11/2001 | Ben-Haim et al. ...... 600/424 |
| 6,347,240 B1 * | 2/2002 | Foley et al. ............. 600/426 |
| 6,390,982 B1 | 5/2002 | Bova et al. |

OTHER PUBLICATIONS

Barth, Norman H. "An Inverse Problem in Radiation Therapy." *Int. J. Radiation Oncology, Biol., Phys.* V. 18, No. 2. Feb. 1990. pp. 425–431.

* cited by examiner

Primary Examiner—Marvin M. Lateef
Assistant Examiner—Jeoyuh Lin
(74) Attorney, Agent, or Firm—Miles & Stockbridge; Dennis P. Clarke

(57) ABSTRACT

A computer controlled system for guiding the needle device, such as a biopsy needle, by reference to a single mode medical imaging system employing any one of computed tomography imaging (CTI) equipment, magnetic resonance imaging equipment (MRI), fluoroscopic imaging equipment, or 3D ultrasound system, or alternatively, by reference to a multi-modal imaging system, which includes any combination of the aforementioned systems. The 3D ultrasound system includes a combination of an ultrasound probe and both passive and active infrared tracking systems so that the combined system enables a real time image display of the entire region of interest without probe movement.

29 Claims, 2 Drawing Sheets

COMPUTER CONTROLLED GUIDANCE OF A BIOPSY NEEDLE

BACKGROUND OF THE INVENTION

The present invention relates generally to interventional medicine, and particularly concerns properly locating, vectoring, and inserting a needle-like medical device toward and into a targeted patient anatomic feature while the patient is being imaged with single, or multi-modality medical imaging equipment such as computed tomography imaging (CTI) equipment, magnetic resonance imaging equipment (MRI), fluoroscopic imaging equipment, and 3D ultrasound equipment.

Among others, Frank J. Bova and William A. Friedman of the present inventors have pioneered the art of high precision planning and treatment of intracranial targets using radiation originating from medical linear accelerators. All of these previously developed planning and treatment systems have been based upon a rigid model consisting of the patient's skull, upper dentisia and intracranial anatomy. Exemplary of these systems and methods are those described in U.S. patent application Ser. No. 09/621,868, filed Jul. 21, 2000, and in the following U.S. Pat. Nos., all issued to the Bova and Friedman on the indicated dates, assigned to the assignee of the present application, the entire contents and disclosures of all of which are incorporated herein by reference:

| | | |
|---|---|---|
| 5,954,647 | Marker system and related stereotactic procedure | Sep. 21, 1999 |
| 5,588,430 | Repeat fixation for frameless stereotactic procedure | Dec. 31, 1996 |
| 5,189,687 | Apparatus for stereotactic radiosurgery | Feb. 23, 1993 |
| 5,027,818 | Dosimetric technique for stereotactic radiosurgery | July 02, 1991 |

Although this rigid model is valid for cranial targets, it is not practical for all anatomic regions. An example of a target that cannot be modeled with a rigid body modality is metastatic disease within the liver. In order to effect the application of high precision biopsy, radiation treatments or other medical procedures to such deformable anatomic regions, real time imaging of the target region must be incorporated into the treatment procedure.

Multiplanar x-rays and ultrasound are the best suited of all of the modalities available for such real time imaging. Multiplanar x-ray imaging, primarily orthogonal imaging, has been used to localize radiation targets for several decades. While this mode of target localization has several advantages, its primary disadvantages are the space and time it requires. The space required by the imaging chain, including x-ray source(s) and imaging electronics, is simply not available near or around a patient who is in position for real time treatment, especially if the treatment uses a medical linear accelerator. Depending on how fast an image of a given portion of the anatomy changes with time and the time required to complete a multiplanar x-ray process, the x-ray imaging may not be sufficiently fast to track changes and provide accurate real time data.

U.S. Pat. No. 5,893,832, issued to Song on Jun. 24, 1997, describes an ultrasound probe which provides a 3D image of an anatomic region without external probe movement. The probe effectively provides a 3D image of a selected anatomic region without the necessity for external probe movement. Ultrasound probes like those of the Song patent can provide real time imaging of a portion of the patient's anatomy, although the image data is with reference to the position of the ultrasound probe. As the ultrasound probe is moved, the point of reference changes.

U.S. patent application Ser. No. 09/621,868, filed Jul. 21, 2000 describes a system which enables image guidance during radiation therapy and surgery, by combining an ultrasound probe with both passive and active infrared tracking systems for production of a 3D image. The combined system enables a real time image display of the entire region of interest without probe movement. The system enables probe displacement during image acquisition so that all external displacements introduced by the probe can be accounted for at the time of placement of elements in support of a treatment protocol. This is accomplished by registration of a patient's real world anatomy with the patient's virtual world imaging study. The coordination of these two worlds allow for a clinician to perform a procedure in the virtual world and then, with the aid of computer guidance execute the procedure in the real world.

The first application of linking the real world with the virtual world was the establishment of stereotactic neurological procedures based upon rigid stereotactic frames. Frameless virtual guidance technology has also been established for several operative environments. Intracranial procedures, based upon CTI and or MRI scans have been available for several years. The same CTI or MRI based guidance have also been available for planning and guidance in spinal surgery. Recently, imaging support for the virtual environment has been extended to include virtual fluoroscopy. At the University of Florida the incorporation of both 2D and 3D ultrasound has now been made available for virtual procedures. This form of guidance is employed in many daily procedures including brain tumor biopsy, brain tumor resection, deep brain stimulation, pallidotomy for Parkinson's disease, lesioning procedures for pain, pedicle screw fixation, guidance for ENT surgical procedures, radiosurgery and stereotactic radiotherapy.

What is needed, is the extension of this technology to image guidance during biopsy. It is desirable to reapply the tools used to project a virtual surgical, or radiation, tool to a biopsy needle. More particularly, it is desirable to apply CTI, MRI, fluoroscopy and ultrasound procedures, either independently or in combination, i.e., multi modality imaging, to guidance and placement of a biopsy needle.

SUMMARY OF THE INVENTION

The present invention is described in terms of two embodiments, the first of which is a computer controlled system for guiding a needle device, such as a biopsy needle, by reference to a single mode medical imaging system employing any one of computed tomography imaging (CTI) equipment, magnetic resonance imaging equipment (MRI), fluoroscopic virtual imaging equipment, or 3D ultrasound equipment. The second embodiment is a computer controlled system for guiding the needle device by reference to a multi-modal system, which includes any combination of the above-listed systems.

In the first embodiment, the method of the present invention includes use of a needle device 3D image data set including 3D geometry of the needle device in conjunction with a data set obtained from a single image system, wherein the needle device is configured to be carried by a needle device carrier. The needle device carrier is configured to move in orthogonal coordinate directions relative to a fixed frame of reference so that a current digital positional description of the needle device carrier can be identified with respect to the fixed frame of reference, which is with reference to the real world patient's position.

A broad description of the first embodiment is directed to the steps of imaging at least a portion of a patient with an imaging device to provide a set of patient imaging data, the set of patient imaging data having a fixed frame of reference relative to the patient, combining an image of the needle device with the set of patient imaging data to provide a combined image data set, calculating a desired combined image data set corresponding to a desired position of the needle device relative to the patient and the fixed frame of reference and causing relative movement between the patient and the needle device, based on the desired combined image data set, to bring the needle device position data set into registry with the desired position of the needle device.

In a more detailed description of the first embodiment, the method includes the step of securing a plurality of patient position markers fixed relative to a patient, the patient position markers defining a fixed frame of reference. At least a part of the patient is imaged using an imaging device to provide a set of patient imaging data, the set of patient imaging data being relative to the fixed frame of reference. The set of patient imaging data includes positional data of the patient position markers when the patient position markers are image-conspicuous, and, alternatively, combined with telemetry fiduciary data when telemetry readouts are arranged to correspond to successive positions of a patient to be scanned. The set of patient imaging data is 3D data derived from 3D imaging systems, including virtual fluoroscopic and 3D ultrasound imaging systems, as well as CTI and MRI imaging systems, and any other 3D system to be developed.

The current position description of the needle device carrier is identified with respect to the fixed frame of reference and a needle position data set is calculated with respect to the fixed frame of reference. A composite data set is calculated by combining the needle device 3D image data set and the 3D patient image data set, wherein the needle device 3D image data set is adjusted with respect to the fixed frame of reference according to the needle position data set. The composite data set is determined from a selected set of co-ordinate locations defining a carrier guide path for movement of the needle device carrier with respect to the fixed frame of reference. The selected set of co-ordinate locations is applied to the needle device carrier so that the needle device moves along a desired needle device guide path corresponding to the carrier guide path.

As in the broad description of the first embodiment, the imaging device of the more detailed description is selected from a group of imaging devices including a computerized tomography imaging device, an magnetic resonance imaging device, a fluoroscopic imaging device, and a 3D ultrasound imaging device that produces 3D imaging data without relative movement between the ultrasound imaging device and the patient. Additionally, the needle device is selected from a group of needle devices including a biopsy needle, a needle configured for injection of toxin into diseased tissue, and an instrument configured for precision placement of a screw, such as a pedicle screw, and the needle device 3D image data set is selected from a group of 3D image data sets including a biopsy needle 3D image data set, an injection needle 3D image data set, and an instrument 3D image data set.

In one embodiment, the patient position markers are secured directly to the patient, and in a separate embodiment, the patent position markers are secured to the scanner table, which supports the patient. Alternatively, the patient position is determined by telemetry.

In the second embodiment of the present invention, there is provided a method and system for properly locating, vectoring, and inserting a needle device toward and into a targeted patient anatomic feature, including imaging at least a portion of a patient with a first imaging technique to provide a first set of imaging data, the first set of imaging data having a fixed frame of reference. In one form of the second embodiment, a second set of imaging data is obtained by a second imaging technique to provide a second set of imaging data, preferably after the first imaging technique is complete. The data sets obtained from the two techniques are then combined to provide a composite data set. Advantageously, if the second imaging technique is both operatively faster and more conducive to the patient treatment environment than the first technique, but is less discriminating than the first imaging technique in terms of image detail, the application of the second imaging data set, as obtained on a substantially real time basis, can be used to update, and effectively determine, a desired selected view obtained from a stored data set from the more detailed first imaging technique.

In a second form of the second embodiment of the present invention, after the above-described first set of imaging data has been obtained, at least a part of the patient is imaged with a second imaging technique which uses an ultrasound device to provide a second set of imaging data, the second set of imaging data being 3D data relative to the ultrasound device and not being fixed relative to the fixed frame of reference. The ultrasound device is operable to provide the 3D data without relative movement between the ultrasound device and the patient, as described in copending U.S. patent application Ser. No. 09/621,868. Position data is determined for the ultrasound device. Using the determined position data and the second set of imaging data, a converted set of imaging data corresponding to the second set of imaging data being referenced to the fixed frame of reference is provided. The converted set of image data is combined with at least some of the first set of imaging data to provide a first composite set of imaging data. An image of the needle device is provided. The image of the needle device is combined with the first composite set of image data to produce a second composite set of image data.

In the second composite set of imaging data the position and orientation of the image of the needle device is identified relative to the image of the at least a portion of the patient and a desired position and orientation of the needle device image corresponding to a desired actual position and orientation of the needle device relative to the patient is determined therefrom. The relative movement between the patient and the needle device is caused to bring the needle device position data set into registry with the desired position and orientation of the needle device.

The first imaging technique, as used to provide the first set of imaging data, is selected from the group consisting of computerized tomography imaging, magnetic resonance imaging, and fluoroscopic imaging. In one method of the invention, the first imaging technique is performed and completed prior to the imaging with the ultrasound device.

The step of imaging with the ultrasound device uses an ultrasound probe that produces 3D imaging data without relative movement between the ultrasonic probe and the patient. The step of determining position data for the ultrasound probe includes determining the position of a plurality of probe position markers on the ultrasound probe, the position of the probe position markers being determined by a technique not including the first and second imaging techniques. The position of the ultrasound probe is determined using infrared (IR) imaging In the course of a medical procedure employing the present invention, as applied to a patient, an image of the needle device is used in combination with the converted set of imaging data to achieve positioning of the needle device relative to the patient. The needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

Relative movement is caused between the patient and the needle device to bring the second set of imaging data into registry with the first set of imaging data. Alternatively, the relative movement is accomplished by controlling the needle device with a robotic guidance apparatus.

The method further includes the step of, at least before completion of the first imaging technique, securing a plurality of patient position markers fixed relative to the patient. Alternatively, the patient position markers are secured to a scanner table for supporting the patient, or they are determined by telemetry or infrared (IR) imaging.

The system of the first embodiment of the present invention provides computer controlled guidance of a needle device including a plurality of patient position markers operable for defining a fixed frame of reference relative to a patient, a needle device, a needle device 3D image data set including 3D geometry of the needle device, and a needle device carrier configured for carrying the needle device for relative movement between the patient and the needle device.

The system also includes a 3D imaging system operable for imaging at least a part of the patient to provide a set of patient 3D imaging data, the set of patient 3D imaging data including positional data of the patient position markers representing a fixed frame of reference when the patient position markers are image-conspicuous, and combined with telemetry fiduciary data when telemetry readouts are arranged to correspond to successive positions of a patient to be scanned. A position determiner is provided for identifying a current position description of the needle device carrier with respect to the fixed frame of reference. A first processor is provided for calculating a needle position data set using the current position description, and a second processor is provided for calculating a composite data set by combining the patient 3D image data set and the needle device 3D image data set, wherein the needle device 3D image data set is adjusted with respect to the patient 3D image data set according to the needle position data set. A third processor is provided for calculating from the composite data set a selected set of co-ordinate locations defining a carrier guide path for movement of the needle device carrier with respect to the fixed frame of reference so that the needle device moves along a desired needle device guide path corresponding to the carrier guide path.

The needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

The system of the second embodiment includes a plurality of patient position markers operable for fixing relative to a patient to define a fixed frame of reference, a needle device, a needle device 3D image data set including 3D geometry of the needle device, and a needle device carrier configured for carrying the needle device for relative movement between the patient and the needle device.

The system also includes a non-ultrasonic 3D imaging subsystem operable for imaging at least a portion of the patient to provide a first patient 3D imaging data set, the first patient 3D imaging data set including positional data of the patient position markers representing a fixed frame of reference when the patient position markers are image-conspicuous, and combined with telemetry fiduciary data when telemetry readouts are arranged to correspond to successive positions of a patient to be scanned.

A 3D imaging subsystem operable is provided for imaging at least a part of the patient to provide a second patient 3D imaging data set, the part of the patient including at least some of the at least a portion of the patient, the 3D imaging subsystem being configured to use an ultrasound device to provide a second patient 3D imaging data set, the second patient 3D imaging data set being 3D data relative to the ultrasound device and not being fixed relative to the fixed frame of reference, the ultrasound device being operable to provide the second patient 3D imaging data set without relative movement between the ultrasound device and the patient.

A determiner is provided for determining position data for the ultrasound device, and a second processor is provided for using the determined position data and the second set of imaging data to calculate a converted set of imaging data corresponding to the second patient 3D imaging data set being referenced to the fixed frame of reference. A third processor is provided, the processor being operable for combining the converted set of image data with at least some of the first patient 3D imaging data set to provide a first composite imaging data set.

Also included is a position determiner operable for determining a needle device actual position and orientation data set and a fourth processor is included, the processor being operable for applying the determined needle device actual position and orientation data set to the needle device 3D image data set to form a result and for combining the result with the first composite imaging data set to produce a second composite image data set. The second composite image data set is configured for identification of the position and orientation of the needle device image relative to the first patient 3D imaging data set and determining therefrom a desired position and orientation of the needle device image corresponding to a desired actual position and orientation of the needle device relative to the patient.

Relative movement can be caused between the patient and the needle device to bring the needle device position data set into registry with the desired position and orientation of the needle device, based on the determined desired position and orientation.

As in the first embodiment, the needle device for the second embodiment is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

The non-ultrasonic 3D imaging subsystem is selected from the group consisting of a computerized tomography system, a magnetic resonance system, and a fluoroscopy system. The ultrasound device can be configured to include an ultrasound probe that produces 3D imaging data without relative movement between the ultrasound probe and the patient, and includes the ultrasound probe can include a plurality of probe position markers thereon.

Optionally, the position determiner includes a subsystem to determine the position of the probe position markers and the patient position markers. Further, the system optionally includes an infrared (IR) camera.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
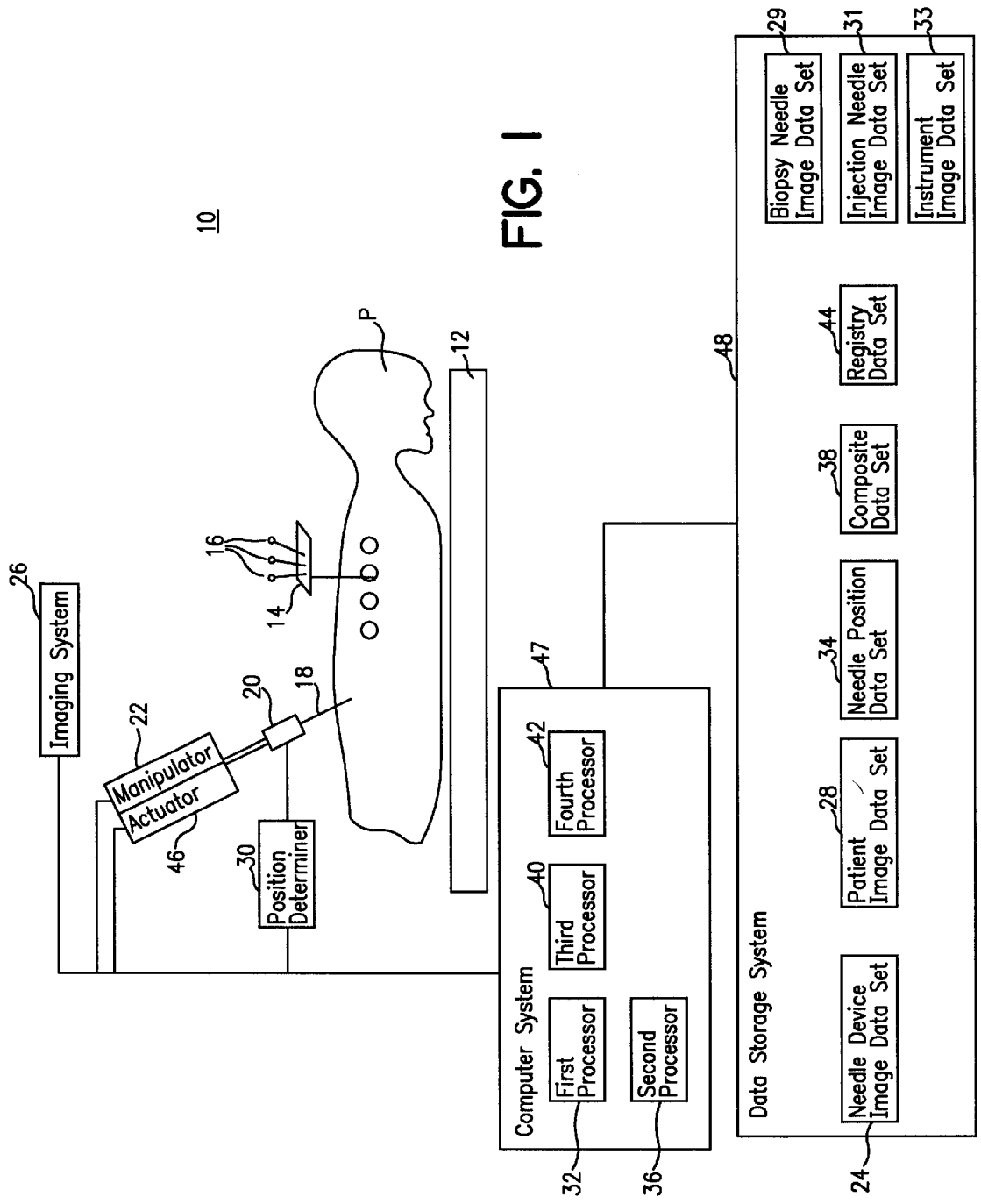
FIG. 1 is a simplified block diagram of the computer controlled system of the present invention shown in relationship to a simplified sectional side view of a patient P.

FIG. 1 is a simplified block diagram of the computer controlled system 10 of the present invention shown in relationship to a simplified sectional side view of a patient P. System 10 is for guiding a needle device, such as a biopsy needle, of the present invention, by reference to a single mode imaging system, which includes any one of computed tomography imaging (CTI) equipment, magnetic resonance imaging equipment (MRI), 3D ultrasound equipment, or virtual fluoroscopic imaging equipment.

Patient P is shown on a table 12 and a position reference device 14 with a plurality of patient position markers 16 thereon. The reference device 14 is preferably secured directly to a stable (such as skeletal) part of the patient. The markers 16 are preferably passive (reflecting devices) or active devices which can be sensed with an infrared (IR) camera (shown in FIG. 2, discussed below). The markers and reference device can be constructed with IR reflectors, IR LEDs and various other components in a known way and are used to define a fixed frame of reference, as discussed in more detail in the various patents herein incorporated by reference. As illustrated, the device is secured to a bone of the patient.

A needle device 18 attached to a needle device carrier 20 configured for carrying needle device 18 for relative movement between patient P and the needle device 18. A manipulator arm 22, which may be either a robotic arm controlled by known methods or an manually manipulated arm, is operatively attached to needle carrier 20.

A needle device 3D image data set 24 is stored in accordance with known data storage techniques and includes a digital depiction of the 3D geometry of the needle device 18.

A 3D imaging system 26, which is operable for imaging at least a part of patient P to provide a set of patient 3D imaging data 28. The set of patient 3D imaging data 28 includes positional data of the patient position markers 16 representing a fixed frame of reference when the patient position markers 16 are image-conspicuous, and can be combined with telemetry fiduciary data derived from a known telemetry system (not shown) when telemetry readouts are arranged to correspond to successive positions of a patient to be scanned.

A position determiner 30 is provided for identifying a current position description of the needle device carrier 20 with respect to the fixed frame of reference.

A first processor 32 is provided for calculating a needle position data set 34 using the current position description, and a second processor 36 is provided for calculating a composite data set by combining the patient 3D image data set 38 and the needle device 3D image data set 24, wherein the needle device 3D image data set 24 is adjusted with respect to the patient 3D image data set 28 according to the needle position data set 34. A third processor 40 is provided for calculating from the composite data set 38 a selected set of co-ordinate locations defining a carrier guide path for movement of the needle device carrier 20 with respect to the fixed frame of reference so that the needle device 18 moves along a desired needle device guide path corresponding to the carrier guide path.

System 10 further includes a fourth processor 42 configured for enabling a user to bring the needle device position data set 34 into registry with the desired position and orientation of the needle device 18, as represented relative to the patient 3D imaging data set 28, to produce a registry data set 44. An actuator 46 responsive to the registry data set 44 is attached to needle carrier 20 for relative movement between the patient P and the needle device 18. Alternatively, actuator 46 and manipulator arm 22 can be the same apparatus.

The needle device 18 is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set 29, an injection needle 3D image data set 31, and an instrument 3D image data set 33.

First processor 32, second processor 36, third processor 40, and fourth processor 42 are computational units which can be software or hardware modules arranged separately or in any appropriate combination as part of a computer system 47. Needle device 3D image data set 24, patient 3D imaging data set 28, needle position data set 34, composite data set 38, and registry data set 44 are data sets 48 which reside on suitable data storage media and are configured for retrieval and update by computer system 47. Computer system 47 is operatively connected to 3D imaging system 64, position determiner 30, and manipulators 22 and 46, as appropriate and in accordance with known practices.

Figure 2:
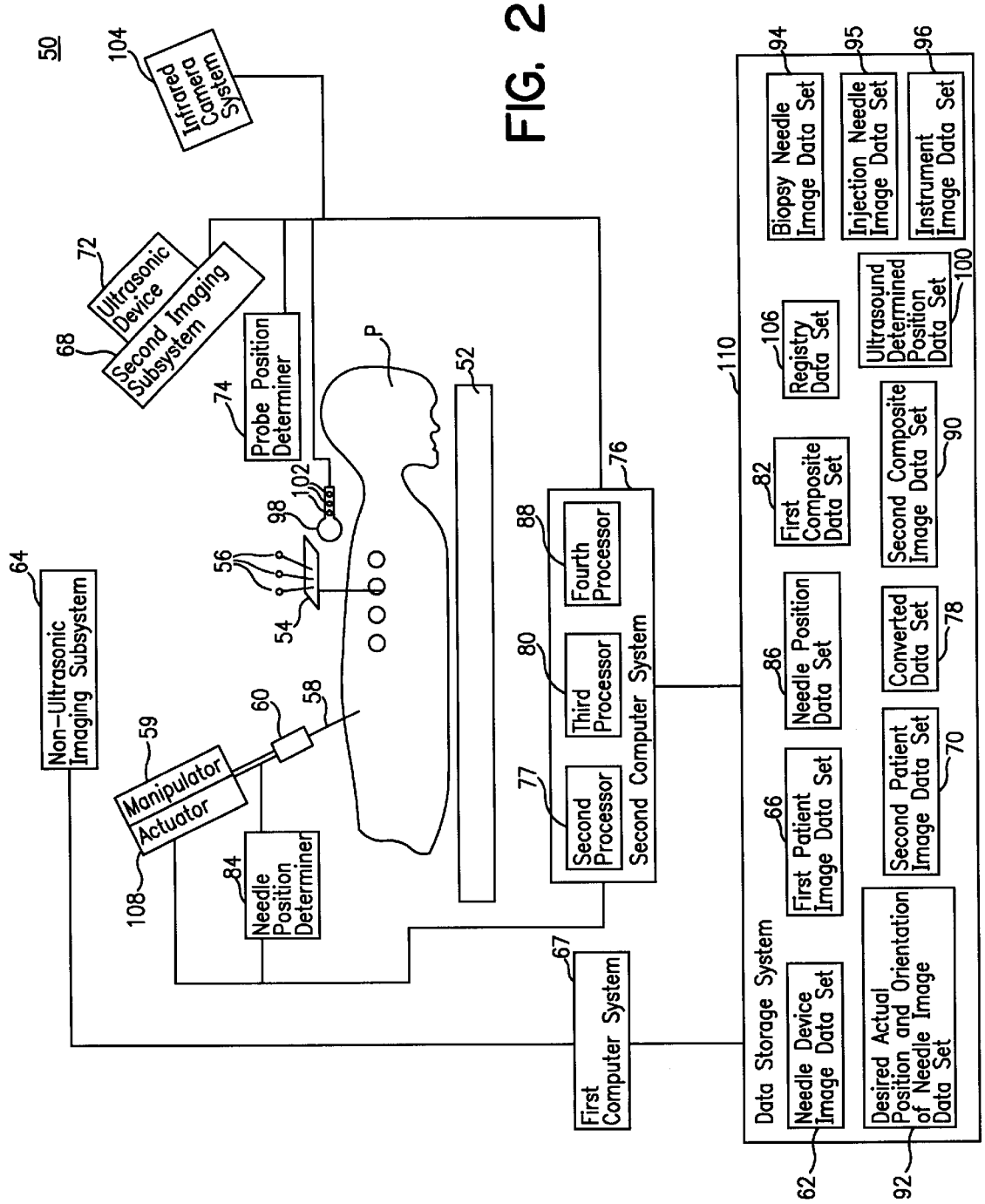
FIG. 2 is a simplified block diagram of a second embodiment of the present invention shown in relationship to a simplified sectional side view of a patient P.

FIG. 2 is a simplified block diagram of a computer controlled system 50 shown in relationship to a simplified sectional side view of a patient P, and illustrating a second embodiment of the present invention, which includes a patient P disposed on a table 52, a position reference 54 associated with a plurality of patient position markers 56 operable for fixing relative to patient P to define a fixed frame of reference, a needle device 58, a needle device carrier 60 configured for carrying needle device 58 for relative movement between patient P and needle device 58, and a needle device 3D image data set 62 including 3D geometry of needle device 58. Optionally, needle device carrier 60 is actuated by a manipulator 59, which is a robotic arm or is operated manually.

System 50 also includes first and second imaging subsystems, which can take the form of any combination of 3D imaging techniques. For illustrative purposes, the preferable combination of a 3D ultrasound imaging subsystem and any other 3D imaging subsystem will be described. In that arrangement, the first subsystem takes the form of a non-ultrasonic 3D imaging subsystem 64 operable for imaging at least a portion of patient P to provide a first patient 3D imaging data set 66. The first patient 3D imaging data set 66 includes positional data of patient position markers 56 representing a fixed frame of reference when the patient position markers 56 are image-conspicuous, and combined with telemetry fiduciary data when telemetry readouts are arranged to correspond to successive positions of a patient to be scanned. Non-ultrasonic 3D imaging subsystem 64 is generally similar to 3D imaging system 26 described in connection with system 10, including operative connections with a first computer system 67.

The second 3D imaging subsystem is subsystem 68, which is provided for imaging at least a part of patient P to provide a second patient 3D imaging data set 70 representing a part of patient P including at least some of the at least a portion of patient P. Although subsystem 68 can be any 3D imaging system, preferably, 3D imaging subsystem 68 is connected to a second computer system 76, including a second processor 77, and is configured to use a 3D ultrasound device 72 to provide the second patient 3D imaging data set 70, the second patient 3D imaging data set 70 being 3D data relative to ultrasound device 72 and not being fixed relative to the fixed frame of reference. The ultrasound device 72 is operable to provide the second patient 3D imaging data set 70 without relative movement between the ultrasound device 72 and patient P, as described in copending U.S. patent application Ser. No. 09/621,868, previously herein incorporated by reference.

The ultrasound imaging data obtained from the 3D ultrasound imaging subsystem 68 is converted to be relative to the fixed frame of reference and is then combined into the imaging data obtained from the non-ultrasonic 3D imaging subsystem 64. The result of the combined data sets are used for targeting needle device 58 to the proper part of patient P. By combining the ultrasound data with the imaging data of subsystem 64 one obtains the value of real time ultrasound data in combination with the higher resolution of the earlier obtained non-ultrasound imaging data set.

A probe position determiner 74 is provided for determining position data 100 for the ultrasound device 72, and second processor 77 is provided for using the determined position data 100 and the second set of imaging data 70 to calculate a converted set of imaging data 78 corresponding to the second patient 3D imaging data set 70 being referenced to the fixed frame of reference.

A third processor 80 is provided, processor 80 being operable for combining the converted set of image data 78 with at least some of the first patient 3D imaging data set 66 to provide a first composite imaging data set 82.

Also included is a needle position determiner 84 operable for determining, for the needle device 58, a needle device actual position and orientation data set 86.

A fourth processor 88 is operable for applying the determined needle device actual position and orientation data set 86 to needle device 3D image data set 62 to form a result and for combining the result with the first composite imaging data set 66 to produce a second composite image data set 90.

The second composite image data set 90 is configured for identification of the position and orientation of needle device image 62 as shown in the overall second composite image data set 90 and determining therefrom a desired position and orientation of the needle device image 92 corresponding to a desired actual position and orientation of the needle device relative to patient P.

Relative movement is caused between patient P and needle device 58 to bring the needle device position data set 86 into registry with the desired position and orientation of the needle device 92, based on the determined desired position and orientation.

As in the first embodiment, needle device 58 for the second embodiment is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set 94, an injection needle 3D image data set 95, and an instrument 3D image data set 96.

The non-ultrasonic 3D imaging subsystem 64 is selected from the group consisting of a computerized tomography system, a magnetic resonance system, and a fluoroscopy system. The ultrasound device 72 is configured to include an ultrasound probe 98 that produces 3D imaging data without relative movement between ultrasound probe 98 and patient P. Ultrasound probe 98 can include a plurality of probe position markers 102 thereon. Probe 102 provides 3D imaging data to processor 76. Reference device 54 is fixed to probe 102 and has probe position markers 56. Reference device 54 is similar in construction to device 14 of system 10 and has markers 56 similar to markers 16. Reference device 54 differs from device 14 in that device 54 may have fasteners (not shown) or otherwise be fixed to the probe 102.

Optionally, position determiner 74 includes a subsystem to determine the position of the probe position markers 102 and the patient position markers 56. Further, the system a tracking system, such as, for example an infrared (IR) camera 104, which is connected to processor 76 and operatively tracks markers 56 and 102 according to techniques described in copending U.S. patent application Ser. No. 09/621,868, previously herein incorporated by reference. Other tracking systems are also suitable.

A module 105 is provided to bring the needle device position data set 86 into registry with the desired position and orientation 92 of the needle device 58 to produce a registry data set 106 and a mechanism 108 responsive to the registry data set 106 and attached to the needle carrier 60 for relative movement between patient P and needle device 58. Actuator 108 and manipulator 59 is the same automated device for actuating needle device carrier 60.

Second processor 77, third processor 80, and fourth processor 88 are computational units which are software or hardware modules arranged separately or in any appropriate combination as part of a computer system 76. Needle device 3D image data set 62, first patient 3D imaging data set 66, second patient 3D image data set 70, converted data set 78, needle position data set 86, first composite data set 82, second composite image data set 90, desired actual position and orientation of needle image data set 92, ultrasound determined position data set 100, and registry data set 106, together with biopsy needle image data set 94, injection needle image data set 95 and instrument 3D image data set 96, are stored in data storage system 110 and are configured for retrieval and update by computer systems 67 and 76.

Computer system 67 is operatively connected to 3D imaging system 64, position determiner 84, and manipulators 59 and 108. Computer system 76 is operatively connected to second 3D imaging system 68, probe position determiner 74, probe 98, and infrared camera system 104, as appropriate and in accordance with known practices.

The operation of the method of the present invention will now be discussed in the context of each 3D imaging technology. For each 3D imaging procedure, the ability to register the imaging modality to the patient's real world position is an absolute requirement before a needle carrier path can be defined. The use of multi modality imaging, through the use of image registration technology, requires only one image data set derived from one image subsystem to be registered between the real and virtual worlds, while all other image data sets derived from other imaging subsystems are then registered to that data set. An example of this technique is the ability to plan a stereotactic biopsy based upon a stereotactic CTI scan and an MRI scan which is not stereotactically taken but registered anatomically to the CTI scan.

Each imaging modality has unique physical characteristics that require unique solutions in order to provide the real world to virtual world linkage. Any combination of these technologies can be co-registered, once their respective data sets are placed in the virtual world. For ease of description, the image acquisition, registration, and application to guidance of a needle device, such as a biopsy needle, will be separately discussed next in connection with each imaging technology.

Computer Tomography Imaging (CTI) Biopsy Subsystem:

The CTI based approach to locating, vectoring, and inserting a needle-like medical device toward, and into, a targeted patient anatomic feature requires that each individual CTI image, or CT slice, be registered to the patient. This in turn requires the definition of CTI room space and patient space and the ability to track one relative to the other. The definition of this space is through a stereotactic fiducial system incorporated into the scanner table, a reference attached to part of the patient's support-immobilization system, or, alternatively, it is through scanner telemetry readouts. In either situation, each pixel of CTI data is mapped into virtual space and becomes part of the patient's virtual image. When the patient is withdrawn from the scanner gantry, the telemetry system tracks the rigid body move, thereby keeping the patient's virtual data set registration to the patient. Simultaneously, the biopsy needle is introduced to the real world and is tracked in the virtual world through a six-degree of freedom tracking system. This tracking is accomplished through one of a variety of tracking technologies, such as, for example, optical tracking, as in the case of either active or passive infrared tracking systems, or magnetically tracking via an articulated arm system.

Prior to performance of the biopsy medical procedure, the biopsy needle is calibrated so that the needle geometry of the biopsy needle is known to the system and is accurately inserted into the virtual world model. Any movement of the biopsy needle in the real world is mirrored in the virtual world. This allows the clinician to plan a trajectory in the virtual world, in a manner similar to virtual surgical planning, and then guide the real world biopsy needle along this planned trajectory. To assist in the alignment of the biopsy several displays are provided to help align the needle in all size degrees of freedom. This alignment assistance is in the form of freehand guidance or is used to control a robotic guidance apparatus. In this later case the required needle movements are decoupled from the scanner room coordinate system and re-coupled to the robotic guidance coordinate system. This is similar to the decoupling that is provided in a radio camera system, wherein decoupling allows feedback to be aligned with the available linear accelerator table controls that rotate in room space, as the patient is setup.

To assist in the alignment and stabilization of the patient beginning with the scanning and continuing through the biopsy process it may be advantageous to provide a system that incorporates both a stereotactic fiducial system and an immobilization system. Several such systems are commercially available and in the development process the strengths and weaknesses of each should be considered.

Magnetic Resonance Imaging (MRI) Biopsy Subsystem

According to the present invention, alternatively, an MRI biopsy system is made to function in a manner directly parallel to the above-described CTI system. Known software image registration techniques are used to combine the MRI and CTI image data sets to allow for both to be simultaneously available when planning in the virtual world.

Fluoroscopic Biopsy Subsystem:

A standalone fluoroscopic biopsy system configured to develop a virtual image is applied to locating, vectoring, and inserting a needle-like medical device toward, and into, a targeted patient anatomic feature resembles known systems used for virtual fluoroscopic navigation for spinal surgery. In the present invention, the x-ray source and the image intensifier are both fitted with fiducials that are tracked. A reference system is rigidly attached to the patient's anatomy, and in the application to spinal surgery, it usually is attached to a specific vertebra, creating a real world patient coordinate system. The geometry of all fluoroscopic views taken are known relative to the specific patient's reference coordinate system.

Once a set of fluoroscopic views that are sufficient for the clinician to appreciate when an acceptable alignment has been achieved, the fluoroscopic source is no longer used. A biopsy needle, with a known geometry and calibration, is introduced into the real world and mathematically inserted into the corresponding pre-recorded fluoroscopic views in the virtual world. While this system does not have the ability to present the clinician with a true 3D description of the patients anatomy, as would be provided if a CTI or MRI model, it does allow for a significant reduction in x-ray exposure to the patient and operating room personnel and also allows for multiple simultaneous virtual real time fluoroscopic view to be evaluated, eliminating the need to hold the needle's position while the fluoroscopic system is realigned.

As with the CT described above, the fluoroscopic system is made to function via a freehand guidance interface or through a robotic interface, with known coupling of a biopsy needle carrier attached to the biopsy needle with a robotic control system. This system can also be jointly coupled to a CTI biopsy needle guidance system. This is accomplished through a rigid relationship between the CTI room reference system and the fluoroscopic patient reference system. In the, combined system both the plane film fluoroscopic views as well as the true 3D anatomy are appreciated in the virtual world planning system.

Ultrasound Biopsy Subsystem:

An image from a 3D ultrasound system is obtained, transferred to a workstation, and then mapped into both room space and virtual room space. The room space is provided through any imaging source, such as a CTI or MRI imaging system. It is assumed that the patient and the room space form a rigid body system, i.e., the room reference system moves with the patient. With the image in virtual space, a biopsy probe, equipped with tracking, is introduced into room space and simultaneously displayed in virtual space. With the tracking of the probe the clinician is able to appreciate the orientation and trajectory of the biopsy probe in six degrees of freedom, relative to the anatomy that is being ultrasonically imaged. Although the assumption of a rigid body arrangement has been made, this assumption is modified if the interface between the ultrasound system and the workstation is sufficiently fast as to allow for the instantaneous update of the virtual image.

Although specific constructions have been presented, it is to be understood that these are for illustrative purposes only. Various modifications and adaptations will be apparent to those of skill in the art. Therefore, the scope of the present invention should be determined by reference to the claims.

What is claimed is:

1. A method for computer controlled guidance of a needle device configured to move in orthogonal coordinate directions relative to a fixed frame of reference in combination with a 3D imaging device, the method comprising the steps of:

imaging at least a portion of a patient with the imaging device to provide a set of patient imaging data, the set of patient imaging data having a fixed frame of reference relative to the patient;

combining an image of the needle device with the set of patient imaging data to provide a combined image data set;

calculating a desired combined image data set corresponding to a desired position of the needle device relative to the patient and the fixed frame of reference; and causing relative movement between the patient and the needle device, based on the desired combined image data set, to bring the needle device position data set into registry with the desired position of the needle device.

2. The method of claim 1 wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

3. The method of claim 2 wherein causing relative movement between the patient and the needle device is accomplished by controlling the needle device with a robotic guidance apparatus.

4. A method for computer controlled guidance of a needle device using a needle device 3D image data set including 3D geometry of a needle device, the needle device being configured to be carried by a needle device carrier, the needle device carrier being configured to move in orthogonal coordinate directions relative to a fixed frame of reference so that a current digital positional description of the needle device carrier with respect to the fixed frame of reference can be identified, the method comprising the steps of:

securing a plurality of patient position markers fixed relative to a patient, the patient position markers defining the fixed frame of reference relative to the patient;

imaging at least a part of the patient using an imaging device to provide a set of patient imaging data, the set of patient imaging data being relative to the fixed frame of reference, the set of patient imaging data including positional data of the patient position markers when the patient position markers are image-conspicuous, and combined with telemetry fiduciary data when telemetry readouts are arranged to correspond to successive positions of a patient to be scanned;

identifying the current position description of the needle device carrier with respect to the fixed frame of reference and calculating a needle position data set with respect to the fixed frame of reference;

calculating a composite data set by combining the needle device 3D image data set and the patient image data set, wherein the needle device 3D image data set is adjusted with respect to the fixed frame of reference according to the needle position data set; and determining from the composite data set a selected set of co-ordinate locations defining a carrier guide path for movement of the needle device carrier with respect to the fixed frame of reference.

5. The method of claim 4 further comprising the step of applying the selected set of co-ordinate locations to the needle device carrier so that the needle device moves along a desired needle device guide path corresponding to the carrier guide path.

6. The method of claim 4 wherein the imaging device is selected from a group of imaging devices including a computerized tomography imaging device, an magnetic resonance imaging device, a fluoroscopic imaging device, or a 3D ultrasound imaging device that produces 3D imaging data without relative movement between the ultrasound imaging device and the patient.

7. The method of claim 4, further comprising the step of causing relative movement between the patient and the needle device to bring the needle device position data set into registry with the determined desired position and orientation of the needle device.

8. The method of claim 4, wherein the patient position markers are selected from a group of markers consisting of patient markers configured to be secured to a scanner table for supporting the patient and patient position markers configured to be secured directly to the patient.

9. The method of claim 4, wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

10. A method for computer controlled guidance of a needle device configured to move in orthogonal coordinate directions relative to a fixed frame of reference, the method comprising the steps of:

imaging at least a portion of a patient with a first imaging technique to provide a first set of imaging data, the first set of imaging data having a fixed frame of reference relative to the patient;

imaging at least a part of the patient with a second imaging technique to provide a second set of imaging data, the part of the patient including at least some of the at least a portion of the patient, the second imaging technique being different than the first imaging technique, the second set of imaging data being data not necessarily being fixed relative to the fixed frame of reference;

registering the second imaging data set with the first imaging data set to provide a first composite set of imaging data;

providing an image data set of the needle device;

combining the image data set of the needle device with the first composite set of image data to produce a second composite set of image data; and identifying in the second composite set of imaging data the position and orientation of the image of the needle device relative to the image of the at least a portion of the patient and determining therefrom a desired position and orientation of the needle device image corresponding to a desired actual position and orientation of the needle device relative to the patient.

11. The method of claim 10, further comprising the step of causing relative movement between the patient and the needle device to bring the needle device position data set into registry with the determined desired position and orientation of the needle device.

12. The method of claim 10 wherein the first imaging technique is selected from a group consisting of computerized tomography imaging, magnetic resonance imaging, and fluoroscopic imaging and the second imaging technique is a 3D ultrasound imaging technique, wherein the first imaging technique is performed and completed prior to commencement of the second imaging technique.

13. The method of claim 10, wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

14. A method for computer controlled guidance of a needle device configured to move in orthogonal coordinate directions relative to a fixed frame of reference, the method comprising the steps of:

imaging at least a portion of a patient with a first imaging technique to provide a first set of imaging data, the first set of imaging data having a fixed frame of reference;

imaging at least a part of the patient with a second imaging technique to provide a second set of imaging data, the part of the patient including at least some of the portion of the patient, the second imaging technique using an ultrasound device to provide a second set of imaging data, the second set of imaging data being 3D data relative to the ultrasound device and not being fixed relative to the fixed frame of reference, the ultrasound device being operable to provide the second set of imaging data without relative movement between the ultrasound device and the patient, wherein the first set of imaging data is obtained prior to acquisition of the second set of imaging data;

determining position data for the ultrasound device;

using the determined position data and the second set of imaging data to provide a converted set of imaging data corresponding to the second set of imaging data being referenced to the fixed frame of reference;

combining the converted set of image data with at least some of the first set of imaging data to provide a first composite set of imaging data;

providing an image data set of the needle device;

combining the image data set of the needle device with the first composite set of image data to produce a second composite set of image data; and identifying in the second composite set of imaging data the position and orientation of the image of the needle device relative to the image of the at least a portion of the patient and determining therefrom a desired position and orientation of the needle device image corresponding to a desired actual position and orientation of the needle device relative to the patient.

15. The method of claim 14, further comprising the step of causing relative movement between the patient and the needle device to bring the needle device position data set into registry with the determined desired position and orientation of the needle device.

16. The method of claim 14 wherein the step of determining position data for the ultrasound probe includes determining the position of a plurality of probe position markers on the ultrasound probe, the position of the probe position markers being determined by a technique not including the first and second imaging techniques.

17. The method of claim 14 wherein the position of the ultrasound probe is determined using infrared (IR) imaging.

18. The method of claim 14 further comprising the step of, at least before completion of the first imaging technique, securing a plurality of patient position markers fixed relative to the patient.

19. The method of claim 14, wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

20. A system for computer controlled guidance of a needle device comprising:

a needle device 3D image data set including 3D geometry of the needle device;

an imaging system operable for imaging at least a part of the patient to provide a set of patient imaging data, the set of patient imaging data having a fixed frame of reference relative to the patient;

a first processor configured for combining the needle device 3D image data set with the set of patient imaging data to provide a combined image data set; and a second processor configured for calculating a desired combined image data set corresponding to a desired position of the needle device relative to the patient and the fixed frame of reference wherein the desired combined image data set is available to cause relative movement between the patient and the needle device to move the needle device to the desired position.

21. A system for computer controlled guidance of a needle device carried by a needle device carrier configured for causing relative movement between a patient and the needle device comprising:

a plurality of patient position markers operable for fixing relative to the patient to define a fixed frame of reference;

a needle device 3D image data set including 3D geometry of the needle device;

an imaging system operable for imaging at least a part of the patient to provide a set of patient imaging data, the set of patient imaging data including positional data of the patient position markers representing a fixed frame of reference when the patient position markers are image-conspicuous, and combined with telemetry fiduciary data when telemetry readouts are arranged to correspond to successive positions of a patient to be scanned;

a position determiner for identifying a current position description of the needle device carrier with respect to the fixed frame of reference;

a first processor for calculating a needle position data set using the current position description;

a second processor for calculating a composite data set by combining the patient image data set and the needle device 3D image data set, wherein the needle device 3D image data set is adjusted with respect to the patient image data set according to the needle position data set; and a third processor for calculating from the composite data set a selected set of co-ordinate locations defining a carrier guide path for movement of the needle device carrier with respect to the fixed frame of reference so that the needle device moves along a desired needle device guide path corresponding to the carrier guide path.

22. The system of claim 21 further comprising a module to bring the needle device position data set into registry with the desired position and orientation of the needle device to produce a registry data set and a mechanism responsive to the registry data set, the mechanism being operatively attached to the needle carrier to cause relative movement between the patient and the needle device.

23. The system of claim 21 wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

24. A system for computer controlled guidance of a needle device carried by a needle device carrier configured for causing relative movement between a patient and the needle device comprising:

a plurality of patient position markers operable for fixing relative to a patient to define a fixed frame of reference;

a needle device 3D image data set including 3D geometry of the needle device;

a non-ultrasonic imaging subsystem operable for imaging at least a portion of the patient to provide a first patient imaging data set, the first patient imaging data set including positional data of the patient position markers representing a fixed frame of reference when the patient position markers are image-conspicuous, and combined with telemetry fiduciary data when telemetry readouts are arranged to correspond to successive positions of a patient to be scanned;

an imaging subsystem operable for imaging at least a part of the patient to provide a second patient imaging data set, the part of the patient including at least some of the at least a portion of the patient, the imaging subsystem being configured to use an ultrasound device to provide a second patient imaging data set, the ultrasound device including an ultrasound probe that produces 3D imaging data without relative movement between the ultrasound probe and the patient, the second patient imaging data set being relative to the ultrasound device and not being fixed relative to the fixed frame of reference, the ultrasound device being operable to provide the second patient imaging data set without relative movement between the ultrasound device and the patient;

a probe position determiner for determining position data for the ultrasound device;

a second processor operable for using the determined position data and the second set of imaging data to calculate a converted set of imaging data corresponding to the second patient imaging data set being referenced to the fixed frame of reference;

a third processor operable for combining the converted set of image data with at least some of the first patient imaging data set to provide a first composite imaging data set;

a position determiner operable for determining a needle device actual position and orientation data set; and a fourth processor operable for applying the determined needle device actual position and orientation data set to the needle device 3D image data set and the first composite imaging data set to produce a second composite image data set, the second composite image data set being configured for identification of a position and orientation of the needle device image and determining therefrom a desired position and orientation of the needle device image corresponding to a desired actual position and orientation of the needle device relative to the patient.

25. The system of claim 24 further comprising a module to bring the needle device position data set into registry with the desired position and orientation of the needle device to produce a registry data set and an actuator responsive to the registry data set and operatively attached to the needle carrier for relative movement between the patient and the needle device.

26. The system of claim 24 wherein the needle device is selected from a group of needle devices including a biopsy needle, a needle configured for injection of toxin into diseased tissue, and an instrument configured for precision placement of a screw, and the needle device 3D image data set is selected from a group of 3D image data sets including a biopsy needle 3D image data set, an injection needle 3D image data set, and an instrument 3D image data set.

27. The system of claim 24 wherein the non-ultrasonic imaging subsystem is selected from the group consisting of a computerized tomography system, a magnetic resonance system, and a fluoroscopy system.

28. The system of claim 24 further comprising a plurality of probe position markers on the ultrasound probe.

29. The system of claim 24 wherein the position determiner includes a subsystem to determine the position of the probe position markers and the patient position markers.

* * * * *